United States Patent [19]
Frenkel

[11] Patent Number: 5,892,090
[45] Date of Patent: Apr. 6, 1999

[54] ORGANIC PEROXIDE STABILIZATION WITH OXIMES

[75] Inventor: Peter Frenkel, Longview, Tex.

[73] Assignee: Witco Corporation, Greenwich, Conn.

[21] Appl. No.: 31,903

[22] Filed: Feb. 27, 1998

[51] Int. Cl.⁶ .................................................. C07C 69/96
[52] U.S. Cl. ............................................................ 558/261
[58] Field of Search ............................................ 558/261

[56] References Cited

U.S. PATENT DOCUMENTS

| | | | |
|---|---|---|---|
| 2,415,971 | 2/1947 | Stevens | 558/261 X |
| 2,491,397 | 12/1949 | Stevens | 558/261 |
| 3,775,341 | 11/1973 | Barter | 558/261 X |
| 5,654,463 | 8/1997 | Abma et al. | 558/261 |
| 5,654,464 | 8/1997 | Abma et al. | 558/261 |

*Primary Examiner*—Michael G. Ambrose
*Attorney, Agent, or Firm*—Scully, Scott, Murphy & Presser

[57] ABSTRACT

Peroxydicarbonate compounds are stabilized against decomposition by the presence of an effective amount of one or more oximes of the general formula

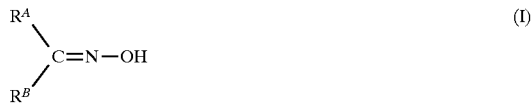

wherein $R^A$ and $R^B$ are optionally substituted alkyl or alkenyl of up to 22 carbon atoms or phenyl, or form a $C_4$–$C_8$ cycloalkyl ring.

20 Claims, No Drawings

ORGANIC PEROXIDE STABILIZATION WITH OXIMES

FIELD OF THE INVENTION

The present invention relates to organic peroxide compositions, and more specifically to peroxydicarbonate compositions, in which one or more oximes has been added to retard the rate of decomposition of the peroxide compound.

BACKGROUND OF THE INVENTION

Organic peroxides, such as peroxydicarbonates, are useful as free-radical initiators in the polymerization or copolymerization of ethylenically unsaturated monomers.

For example, organic peroxides are used as initiators in the polymerization of vinyl halides, such as vinyl chloride or vinyl bromide; vinylidene halides such as vinylidene chloride; and other compounds containing polymerizable unsaturated units. The products of this well known polymerization process have extensive commercial applications.

The polymerization of vinyl halides or the copolymerization of vinyl halides with vinylidene halides is usually conducted in an aqueous medium, i.e., emulsion, solution or suspension polymerization. In such polymerizations, the monomer or mixture of monomers is dispersed in water in the presence of a surfactant and thereafter the polymerization initiated with an organic peroxide. This is a well known reaction that has been widely reported.

All organic peroxides are by their nature hazardous materials. Their usefulness depends on their ability to decompose into free radicals, shown by the following reaction:

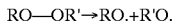

The rate of this decomposition reaction at any given temperature depends on the structure of R and R'.

The decomposition reaction is exothermic. If exothermic decomposition were to occur during production, storage, or shipment, when the peroxides are in a concentrated form, excess pressure development and/or fire or explosion could result. Consequently, many organic peroxides must be kept refrigerated.

There have been several reports in recent years of the retardation of the rate of decomposition of organic peroxides.

The Journal of the American Chemical Society, Volume 72, pages 1254 to 1263 (1950) discloses the use of, for example, ethyl acetoacetate, iodine, trinitrobenzene, acetanilide, nitromethane, phenol, hydrogen peroxide, and tetralin to retard the rate of decomposition of diisopropyl peroxydicarbonate.

U.S. Pat. No. 4,515,929 (1985) reports aqueous dispersions of organic peroxides including peroxydicarbonates, which are stabilized against decomposition by the addition of diphenyl peroxydicarbonate or di(alkyl substituted) phenyl peroxydicarbonates.

U.S. Pat. No. 4,552,682 (1985) discloses the use of phenolic antioxidants to retard the rate of degradation of aqueous organic peroxide dispersions. The use of phenolic antioxidants is undesirable because they result in discoloration.

U.S. Pat. No. 5,155,192 (1992) discloses the use of organic hydroperoxides, e.g., tert-butyl hydroperoxide, to retard the rate of decomposition of peroxydicarbonates.

U.S. Pat. Nos. 5,548,046 (1996) and 5,541,151 (1996) disclose the thermal stabilization of dialkyl peroxydicarbonates using unsaturated nitrites or unsaturated acetylenic compounds.

SUMMARY OF THE INVENTION

The present invention relates to the use of certain non-peroxide compounds which are effective in retarding the rate of decomposition of organic peroxides such as peroxydicarbonates. Thus, one aspect of the present invention is a composition containing an organic peroxide compound, such as a peroxydicarbonate, and one or more oximes which reduces the rate of decomposition of the peroxide compound. Another aspect of the present invention is the method of stabilizing a peroxydicarbonate against decomposition, comprising adding thereto one or more oximes in an amount effective to achieve said stabilization.

The oximes useful in this invention include those of the formula (I)

wherein $R^A$ and $R^B$ are independently of each other hydrogen; branched or unbranched, substituted or unsubstituted, alkyl containing 1 to 22 carbon atoms or alkenyl containing 2 to 22 carbon atoms; phenyl; or substituted phenyl; or $R^A$ and $R^B$ taken together with the carbon atom to which they are attached can form a substituted or unsubstituted cycloalkyl ring containing 4 to 8 carbon atoms; or $R^A$ can be $—C(R^C)=N—OH$ wherein $R^C$ can be hydrogen; branched or unbranched, substituted or unsubstituted, alkyl containing 1 to 22 carbon atoms or alkenyl containing 2 to 22 carbon atoms; phenyl; or substituted phenyl; or $R^C$ taken together with $R^B$ and the carbon atom to which $R^B$ is attached can form a substituted or unsubstituted cycloalkyl ring containing 4 to 8 carbon atoms.

DETAILED DESCRIPTION OF THE INVENTION

The present invention relates to compositions containing an organic peroxide, such as a peroxydicarbonate, and one or more oximes to retard the rate of decomposition of the peroxide compound.

In the foregoing formula (I), the $R^A$ and $R^B$ groups (and the cycloalkyl group which $R^A$ and $R^B$ can cooperate to form) can be substituted or unsubstituted. When substituted, preferred substituents include phenyl, hydroxyl, acyl containing 1 to 4 carbon atoms, alkoxy containing 1 to 4 carbon atoms, ethers, esters containing a total of 1 to 4 carbon atoms, aldehydes containing 1 to 4 carbon atoms, ketones containing 1 to 4 carbon atoms, nitro, or halogen (of which fluoro and chloro are preferred). The hydrocarbon substituents can be branched or unbranched.

Preferred oximes include acetone oxime $R^A=R^B=CH_3$), acetaldoxime ($R^A=H, R^B=CH_3$), 2-heptanone oxime ($R^A=CH_3, R^B=n-C_5H_{11}$) and 4-methyl-2-pentanone oxime ($R^A=CH_3, R^B=(CH_3)_2CHCH_2—$). Other preferred oximes include 2-butanone oxime, cyclohexanone oxime, 1,2-cyclohexanedione dioxime, dimethylglyoxime, and 4-fluorobenzaldoxime.

Liquid oxime can be added directly. Solid oxime can be dissolved in inexpensive solvents and then added to the organic peroxide. Solvents useful in this regard include alcohols, such as methanol, ethanol, or 2-propanol; ethers, such as 2-methoxyethyl ether; glycols, such as ethylene glycol; esters, such as ethyl acetate; and ketones, such as methyl ethyl ketone and diethyl ketone.

The amount of oxime to use in the compositions of the present invention is an amount sufficient to retard the rate of decomposition of the peroxide compound. The preferred amount of oxime is a concentration of 0.2 to 5.0% by weight of the peroxydicarbonate or other organic peroxide present. When the oxime is added as a solution, the amount of the solution to use is adjusted according to the amount of oxime present in the solution. The exact amount will vary and depend on the organic peroxide compound, and on the conditions to which the peroxide composition is to be exposed.

Peroxide compounds useful in this invention are of the general structural formula:

wherein $R^1$ and $R^2$ can each be an aliphatic, cycloaliphatic or aromatic group with 1 to 22 carbon atoms, preferably 2 to 8 carbon atoms. $R^1$ and $R^2$ may be branched or non-branched, substituted or unsubstituted alkyl, alkenyl, cycloalkyl or aromatic groups.

Examples of $R^1$ and $R^2$ groups include phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

Specific examples of peroxydicarbonates include diethyl peroxydicarbonate, di-n-butyl peroxydicarbonate, diisobutyl peroxydicarbonate, and di-4-tert-butylcyclohexyl peroxydicarbonate. Preferably the peroxydicarbonate is di-sec-butyl peroxydicarbonate, di-2-ethylhexyl peroxydicarbonate, di-n-propyl peroxydicarbonate or diisopropyl peroxydicarbonate.

The peroxide compound may be symmetrical or unsymmetrical i.e., $R^1$ and $R^2$ may be the same or different. The peroxide may be a homogeneous mixture containing symmetric peroxides, asymmetric peroxides such as isopropyl-sec-butyl peroxydicarbonate, or a mixture of symmetric and asymmetric peroxides such as mixtures of diisopropyl peroxydicarbonate, di-sec-butyl peroxydicarbonate and isopropyl-sec-butyl peroxydicarbonate as disclosed in U.S. Pat. No. 4,269,726.

The peroxydicarbonate compounds can be synthesized by conventional techniques familiar to one of ordinary skill in the art. Peroxydicarbonates are typically prepared by reacting the corresponding alkyl chloroformate with aqueous sodium peroxide at low temperatures, 0°–20° C. See U.S. Pat. No. 2,370,588 and the Journal of the American Chemical Society, Volume 72, page 1254 (1950). Other synthetic techniques will be familiar to one of ordinary skill in the art.

Preferably, the peroxydicarbonates useful in this invention include those which are a liquid at 0° C. and more preferably a liquid at −5° C. Still more preferred are the peroxydicarbonates which are liquid down to −20° C.

The present invention is especially applicable to aqueous dispersions of peroxydicarbonates that are useful as initiators in the free radical polymerization of ethylenically unsaturated materials, particularly in an aqueous medium, e.g., suspension or emulsion polymerization. A dispersion of the peroxydicarbonate is prepared by dispersing it in water with a suitable dispersing aid, e.g., a surfactant or emulsifying agent. Surfactants and emulsifying agents useful in the formation of such dispersions are well known in this field and are quite numerous.

To prepare dispersions in accordance with the present invention, the oxime or a solution thereof may be added to an already-formed peroxide dispersion, or to the water containing the surfactant, or to the peroxide before the dispersion is formed. Dispersions of the present invention generally contain 20 to 70% by weight, preferably 30 to 60% by weight of the peroxydicarbonate or other organic peroxide compound and 0.2 to 5.0% (by weight of the peroxide) of oxime.

The manner of preparation of peroxide dispersions is known to one of ordinary skill in the art. A description of peroxydicarbonate dispersions and their preparation can be found in U.S. Pat. No. 4,515,929; U.S. Pat. No. 3,825,509; U.S. Pat. No. 3,988,261 and U.S. Pat. No. 4,092,470.

Peroxydicarbonate compositions of the present invention may also be prepared as physical mixtures in the form of liquids, granules, powders or flakes. A physical mixture in accordance with the present invention may be prepared by mixing a liquid peroxide compound, or a solution of a peroxide in a suitable solvent, with the desired amount of a liquid oxime or a solution thereof in a suitable solvent in a conventional mixing apparatus. The resulting mixture is then, if desired, granulated, pulverized or flaked. The oxime may be added either (1) to the chloroformate-containing reaction mixture before preparation of the peroxide compound or (2) to the unprocessed reaction mixture immediately after preparation of the peroxide compound. Either (1) or (2) will ensure that the two components are mixed as homogeneously as possible in order to receive the greatest possible benefit from the stabilizing effect of the oxime.

A solution of the present invention may be prepared by combining the desired amounts of oxime and peroxide in a suitable solvent.

Suitable organic solvents include those normally employed for peroxydicarbonates such as esters of phthalic acid, an example of which is dibutyl phthalate, and aliphatic and aromatic hydrocarbons and mixtures of such hydrocarbons, examples of which are hexane, odorless mineral spirits, mineral oil, benzene, toluene, xylene and (iso) paraffins such as isododecane. Other suitable solvents will be familiar to one of ordinary skill in the art.

Solutions according to the present invention preferably contain at least 10% by weight and more preferably at least 25% by weight of a peroxydicarbonate compound.

The peroxide compositions of the present invention display numerous significant advantages. Chief among these is improved thermal stability, both in response to exposure to elevating temperature and in response to a given constant temperature.

Thermal stability of self-reactive substances, in response to elevating temperatures, can be determined by measuring the self accelerating decomposition temperature or SADT. SADT is one of the recognized tests to determine the safe storage and transportation of materials such as organic peroxides. [Recommendations on the Transport of Dangerous Goods, 9th ed, United Nations, NY 1995, Section 11.3.5, page 264].

SADT can be directly correlated with the onset temperature as measured in a differential thermal analyzer (DTA). The onset temperature is the point at which an uncontrolled thermal decomposition starts. The onset temperature can be measured by determining the point at which the rate of temperature increase in a sealed cell exceeds a certain predetermined value. In addition, the onset temperature can be measured by determining the point at which the rate of pressure increase in the sealed cell exceeds a certain predetermined value.

Thermal stability in response to a given constant temperature can be assessed by means of accelerated aging tests at, for instance, 15° C.

The presence of the oxime in accordance with the present invention increases the onset temperature of peroxydicarbonates. Also, the oxime does not detract from the effectiveness of the peroxide as a polymerization initiator.

The following examples are intended to illustrate the claimed invention and are not in any way designed to limit its scope. Numerous additional embodiments within the scope and spirit of the claimed invention will become apparent to those skilled in the art.

EXAMPLE 1

The onset temperature was measured for samples of pure di-2-ethylhexyl peroxydicarbonate, di-2-ethylhexyl peroxydicarbonate diluted in odorless mineral spirits (OMS), and di-sec-butyl peroxydicarbonate diluted in OMS. The onset temperature was also measured for the aforementioned peroxydicarbonate samples in the presence of various amounts of several oximes. The liquid mixtures were prepared by dissolving the required amount of oxime solution in the peroxydicarbonate.

Using a type of Differential Thermal Analyzer (Radex Solo Thermal Analyzer, marketed by Astra Scientific International, Pleasanton, Calif.), with an isothermal hold temperature of 30° C. for 15 minutes and then a temperature increase of 1°/minute to 130° C., the onset temperature was measured for a one gram sample of the peroxydicarbonate in a sealed cell. The onset temperature was measured both by noting the point where the rate of increase ($\Delta T$) of the sample temperature reached 0.2° C./minute and also, independently, the point where the rate of increase in pressure ($\Delta P$) of the closed sample cell reached 1.0 psi/minute. $\Delta T$ is the difference between the oven temperature and the sample temperature. $\Delta P$ is the difference between a reference pre-calibrated pressure and the pressure developed in the sealed sample cell.

Table I presents the results of the tests carried out with samples of pure di-2-ethylhexyl peroxydicarbonate without oxime and with, in turn, acetaldoxime, 2-heptanone oxime, 4-methyl-2-pentanone oxime, and a 50 wt. % solution of acetone oxime in 2-propanol.

Table II presents the results of similar tests carried out with samples of di-2-ethylhexyl peroxydicarbonate in OMS.

Table III presents the results of similar tests carried out with samples of di-sec-butyl peroxydicarbonate in OMS.

The results show that the presence of oxime increases the temperature at which self accelerating decomposition of the peroxydicarbonate will begin. This shows that the oxime is an effective stabilizer. The data also show that the effect is concentration dependent, with the decomposition beginning at a higher temperature when more oxime is present.

TABLE I

Onset Temperature of Decomposition for 97.2% Di-2-ethylhexyl Peroxydicarbonate Unstabilized and Stabilized with Oxime

| Additive | Wt. % of Pure Additive | Onset Temperature (C.°) by $\Delta T$ | by $\Delta P$ |
|---|---|---|---|
| None | 0.0 | 36.7 | 41.0 |
| Acetaldoxime | 0.3 | 41.9 | 45.5 |
| Acetaldoxime | 0.6 | 45.8 | 48.7 |
| Acetaldoxime | 1.0 | 48.2 | 50.7 |

TABLE I-continued

Onset Temperature of Decomposition for 97.2% Di-2-ethylhexyl Peroxydicarbonate Unstabilized and Stabilized with Oxime

| Additive | Wt. % of Pure Additive | Onset Temperature (C.°) by $\Delta T$ | by $\Delta P$ |
|---|---|---|---|
| Acetaldoxime | 2.0 | 49.8 | 51.3 |
| Adetaldoxime | 3.0 | 51.4 | 54.4 |
| Acetaldoxime | 5.1 | 53.3 | 56.3 |
| 2-Heptanone oxime | 2.0 | 47.7 | 50.7 |
| 4-Methyl-2-pentanone oxime | 1.9 | 47.3 | 50.3 |
| Acetone oxime-50* | 0.5 | 42.7 | 44.2 |
| Acetone oxime-50* | 1.5 | 49.0 | 50.1 |
| Acetone oxime-50* | 2.5 | 50.5 | 52.0 |

*Acetone oxime was added as 50 wt. % solution in 2-propanol

TABLE II

Onset Temperature of Decomposition for 74.9% Solution of Di-2-ethylhexyl peroxydicarbonate in OMS Unstabilized and Stabilized by Oxime

| Additive | Wt. % of Pure Additive | Onset Temperature (°C.) by $\Delta T$ | by $\Delta P$ |
|---|---|---|---|
| None | 0.0 | 38.9 | 43.6 |
| Acetaldoxime | 0.3 | 45.8 | 47.7 |
| Acetaldoxime | 0.5 | 48.1 | 49.9 |
| Acetaldoxime | 1.0 | 50.2 | 51.6 |
| Acetaldoxime | 2.0 | 51.1 | 52.2 |
| Acetaldoxime | 3.0 | 53.9 | 54.5 |
| Acetaldoxime | 5.0 | 55.6 | 54.6 |
| 2-Heptanone oxime | 2.0 | 50.1 | 51.4 |
| 4-Methyl-2-pentanone oxime | 2.0 | 49.0 | 50.3 |
| Acetone oxime-50* | 0.5 | 46.6 | 47.8 |
| Acetone oxime-50* | 1.5 | 49.0 | 50.1 |
| Acetone oxime-50* | 2.5 | 53.1 | 53.5 |

*Acetone oxime was added as 50 wt. % solution in 2-propanol

TABLE III

Onset Temperature of Decomposition for 75.9% Solution of Di-sec-butyl peroxydicarbonate in OMS, Unstabilized and Stabilized by Oxime

| Additive | Wt. % of Pure Additive | Onset Temperature (°C.) by $\Delta T$ | by $\Delta P$ |
|---|---|---|---|
| None | 0.0 | 37.6 | 39.4 |
| Acetaldoxime | 1.1 | 39.8 | 43.5 |
| Acetaldoxime | 3.0 | 47.0 | 47.4 |
| Acetaldoxime | 5.0 | 47.6 | 51.5 |

TABLE III-continued

Onset Temperature of Decomposition for
75.9% Solution of Di-sec-butyl peroxydicarbonate in
OMS, Unstabilized and Stabilized by Oxime

| Additive | Wt. % of Pure Additive | Onset Temperature (°C.) by ΔT | by ΔP |
|---|---|---|---|
| 2-Heptanone oxime | 3.0 | 45.1 | 45.7 |
| 4-Methyl-2-pentanone oxime | 3.1 | 44.6 | 46.4 |
| Acetone oxime-50* | 1.5 | 39.6 | 42.7 |
| Acetone oxime-50* | 2.5 | 42.6 | 44.8 |

*Acetone oxime was added as 50 wt. % solution in 2-propanol

EXAMPLE 2

The effect of the presence of acetaldoxime, representative of the oxime group, on the storage stability at 15° C. of pure di-2-ethylhexyl peroxydicarbonate, di-2-ethylhexyl peroxydicarbonate diluted in odorless mineral spirits (OMS), and di-sec-butyl peroxydicarbonate diluted in OMS, was determined as an accelerated aging test. The purity (active oxygen content) of the peroxydicarbonate was measured after 4, 11, 18 and 25 days. The results, presented in Table IV, show that the oxime is an effective stabilizer of peroxydicarbonates. The initial purity values were corrected for the presence of the oxime additive.

TABLE IV

Purity vs. Time at 15° C. for Peroxydicarbonates Stabilized with Acetaldoxime

| Peroxide | Wt. % of Additive | Start | 4 days | 11 days | 18 days | 25 days |
|---|---|---|---|---|---|---|
| 97.2% Di-2-ethylhexyl peroxy-di-carbonate (pure) | None | 97.2(100) | 47.7(49.1) | 22.6(23.3) | 14.3(14.7) | 10.3(10.6) |
| | 0.5 | 96.7(100) | 89.8(92.9) | 55.5(57.4) | 29.4(30.4) | 18.6(19.2) |
| | 1.0 | 96.2(100) | 90.4(94.0) | 73.1(76.0) | 42.1(43.8) | 25.6(26.6) |
| | 3.0 | 94.4(100) | 86.4(91.5) | 80.7(85.5) | 71.3(75.5) | 55.8(59.1) |
| 74.9% Di-2-ethyl-hexyl Peroxy-di-carbonate in OMS | None | 74.9(100) | 39.0(52.1) | 16.6(22.2) | 9.8(13.1) | 6.7(8.9) |
| | 0.5 | 74.6(100) | 66.7(89.4) | 45.5(61.0) | 24.3(32.6) | 14.4(19.3) |
| | 1.0 | 74.2(100) | 68.8(92.7) | 56.8(76.5) | 38.5(51.9) | 25.3(34.1) |
| | 3.0 | 72.7(100) | 65.6(90.2) | 59.3(81.6) | 53.1(73.0) | 43.7(60.1) |
| | 5.0 | 71.4(100) | 61.5(86.1) | 55.0(77.0) | 50.9(71.3) | 45.7(64.0) |
| 75.9% di-sec-butyl Peroxydi-carbonate in OMS | None | 75.9(100) | 34.1(44.9) | 5.6(7.4) | 1.3(1.7) | 0.9(1.2) |
| | 0.5 | 75.5(100) | 47.7(63.2) | 13.4(17.7) | 4.8(6.4) | 3.9(5.2) |
| | 1.0 | 75.1(100) | 56.0(74.6) | 21.2(28.2) | 8.1(10.8) | 4.8(6.4) |
| | 3.0 | 73.6(100) | 65.2(88.6) | 48.2(65.5) | 30.3(41.2) | 17.6(23.9) |

*Percent of non-decomposed material relative to the initial amount of product is in parenthesis.

What is claimed is:

1. A composition comprising:
   a. an organic peroxide component selected from the group consisting of peroxydicarbonate compounds and mixtures thereof; and
   b. a sufficient amount of an oxime of the formula (I) to retard the rate of decomposition of the organic peroxide component

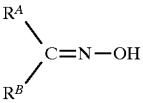

wherein $R^A$ and $R^B$ are independently of each other hydrogen; branched or unbranched, substituted or unsubstituted, alkyl containing 1 to 22 carbon atoms or alkenyl containing 2 to 22 carbon atoms; phenyl; or substituted phenyl; or $R^A$ and $R^B$ taken together with the carbon atom to which they are attached can form a substituted or unsubstituted cycloalkyl ring containing 4 to 8 carbon atoms; or $R^A$ can be —C($R^C$)=N—OH wherein $R^C$ can be hydrogen; branched or unbranched, substituted or unsubstituted, alkyl containing 1 to 22 carbon atoms or alkenyl containing 2 to 22 carbon atoms; phenyl; or substituted phenyl; or $R^C$ taken together with $R^B$ and the carbon atom to which $R^B$ is attached can form a substituted or unsubstituted cycloalkyl ring containing 4 to 8 carbon atoms.

2. A composition according to claim 1 wherein said organic peroxide component comprises at least one compound of the formula

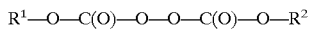

wherein $R^1$ and $R^2$ are independently aliphatic, cycloaliphatic or aromatic groups containing 1 to 22 carbon atoms.

3. A composition according to claim 2 wherein $R^1$ and $R^2$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

4. A composition according to claim 1 wherein said organic peroxide component is selected from the group consisting of diethyl peroxydicarbonate, isopropyl-sec-butyl peroxydicarbonate, di-n-butyl peroxydicarbonate, di-sec-butyl peroxydicarbonate, di-4-tert-butyl cyclohexyl peroxydicarbonate, di-2-ethylhexyl peroxydicarbonate, di-n-propyl peroxydicarbonate, diisopropyl peroxydicarbonate, and mixtures thereof.

5. A composition according to claim 1 wherein said oxime comprises 0.2 to 5.0% by weight of said organic peroxide component.

6. A composition according to claim 2 wherein said oxime is selected from the group consisting of acetone oxime, acetaldoxime, 2-heptanone oxime, 4-methyl-2-pentanone oxime, 2-butanone oxime, cyclohexanone oxime, benzaldehyde oxime, cyclopentanone oxime, 1,2-cyclohexanedione oxime, dimethylglyoxime, and 4-fluorobenzaldoxime.

7. A composition according to claim 2 wherein said oxime is acetone oxime.

8. A composition according to claim 2 wherein said oxime is acetaldoxime.

9. A composition according to claim 2 wherein said oxime is 2-heptanone oxime.

10. A composition according to claim 2 wherein said oxime is 4-methyl-2-pentanone oxime.

11. The method of retarding the rate of decomposition of an organic peroxide product selected from the group consisting of peroxydicarbonate compounds and mixtures thereof, comprising adding to said organic peroxide product an oxime of the formula (I) in an amount thereof effective to retard the rate of said decomposition

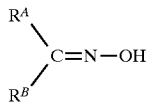
(I)

wherein $R^A$ and $R^B$ are independently of each other hydrogen; branched or unbranched, substituted or unsubstituted, alkyl containing 1 to 22 carbon atoms or alkenyl containing 2 to 22 carbon atoms; phenyl; or substituted phenyl; or $R^A$ and $R^B$ taken together with the carbon atom to which they are attached can form a substituted or unsubstituted cycloalkyl ring containing 4 to 8 carbon atoms; or $R^A$ can be —C($R^C$)=N—OH wherein $R^C$ can be hydrogen; branched or unbranched, substituted or unsubstituted, alkyl containing 1 to 22 carbon atoms or alkenyl containing 2 to 22 carbon atoms; phenyl; or substituted phenyl; or $R^C$ taken together with $R^B$ and the carbon atom to which $R^B$ is attached can form a substituted or unsubstituted cycloalkyl ring containing 4 to 8 carbon atoms.

12. A method according to claim 11 wherein said peroxydicarbonate compounds correspond to the formula $$R^1-O-C(O)-O-O-C(O)-O-R^2$$

wherein $R^1$ and $R^2$ are independently aliphatic, cycloaliphatic or aromatic groups containing 1 to 22 carbon atoms.

13. A method according to claim 12 wherein $R^1$ and $R^2$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

14. A method according to claim 11 wherein said organic peroxide component is selected from the group consisting of diethyl peroxydicarbonate, isopropyl-sec-butyl peroxydicarbonate, di-n-butyl peroxydicarbonate, di-sec-butyl peroxydicarbonate, di-4-tert-butyl cyclohexyl peroxydicarbonate, di-2-ethylhexyl peroxydicarbonate, di-n-propyl peroxydicarbonate, diisopropyl peroxydicarbonate, and mixtures thereof.

15. A method according to claim 11 wherein the amount of said oxime is 0.2 to 5.0% by weight of said organic peroxide product.

16. A method according to claim 12 wherein said oxime is selected from the group consisting of acetone oxime, acetaldoxime, 2-heptanone oxime, 4-methyl-2-pentanone oxime, 2-butanone oxime, cyclohexanone oxime, benzaldehyde oxime, cyclopentanone oxime, 1,2-cyclohexanedione oxime, dimethylglyoxime, and 4-fluorobenzaldoxime.

17. A method according to claim 12 wherein said oxime is acetone oxime.

18. A method according to claim 12 wherein said oxime is acetaldoxime.

19. A method according to claim 12 wherein said oxime is 2-heptanone oxime.

20. A composition according to claim 12 wherein said oxime is 4-methyl-2-pentanone oxime.

* * * * *

UNITED STATES PATENT AND TRADEMARK OFFICE
CERTIFICATE OF CORRECTION

PATENT NO. : 5,892,090
DATED : April 6, 1999
INVENTOR(S) : Peter Frenkel et al.

It is certified that error appears in the above-identified patent and that said Letters Patent is hereby corrected as shown below:

Abstract,
Line 11, "ring." should read -- ring, or $R^3$ is oxime. --

Column 1,
Line 66, "nitrites" should read -- nitriles --

Signed and Sealed this

Sixth Day of November, 2001

Attest:

*Nicholas P. Godici*

NICHOLAS P. GODICI
*Attesting Officer*   Acting Director of the United States Patent and Trademark Office